United States Patent [19]

Tarcha et al.

[11] Patent Number: 5,252,459
[45] Date of Patent: Oct. 12, 1993

[54] INDICATOR REAGENTS, DIAGNOSTIC ASSAYS AND TEST KITS EMPLOYING ORGANIC POLYMER LATEX PARTICLES

[75] Inventors: Peter J. Tarcha, Lake Villa; James J. Donovan, Waukegan; Martin Wong, Grayslake, all of Ill.

[73] Assignee: Abbott Laboratories, Abbott Park, Ill.

[21] Appl. No.: 248,858

[22] Filed: Sep. 23, 1988

[51] Int. Cl.$^5$ ................. G01N 33/546; G01N 33/577
[52] U.S. Cl. ......................................... 435/6; 422/61; 435/7.7; 435/7.71; 435/7.9; 435/975; 436/533; 436/534; 436/548; 436/808
[58] Field of Search ...................... 435/6, 7.4, 975, 7.7, 435/7.71, 7.9; 422/61, 55; 424/78; 436/501, 63, 518, 531, 548, 528, 534, 807, 533, 808

[56] References Cited

U.S. PATENT DOCUMENTS

| | | | |
|---|---|---|---|
| 4,166,820 | 9/1979 | Spallholz . | |
| 4,224,198 | 9/1980 | Renbaum et al. | 436/823 |
| 4,283,382 | 8/1981 | Frank et al. . | |
| 4,292,038 | 9/1981 | Kondo et al. | 436/534 |
| 4,313,734 | 2/1982 | Leuvering . | |
| 4,326,008 | 4/1982 | Ranbaum | 436/501 |
| 4,341,757 | 7/1982 | Spallholz . | |
| 4,373,932 | 2/1983 | Gribnau et al. . | |
| 4,415,700 | 11/1983 | Batz et al. | 436/533 |
| 4,452,886 | 6/1984 | Henry . | |
| 4,656,143 | 4/1987 | Baker et al. | 436/533 |
| 4,678,814 | 7/1987 | Rembaum . | |
| 4,680,274 | 7/1987 | Sakai et al. | 436/518 |
| 4,703,018 | 10/1987 | Craig et al. | 436/533 |
| 4,737,544 | 4/1988 | McCain et al. | 424/78 |
| 4,752,638 | 6/1988 | Nowinski et al. | 436/531 |
| 4,801,504 | 1/1989 | Burdick et al. | 436/534 |
| 4,837,168 | 6/1989 | de Jaeger et al. | 436/534 |
| 4,870,007 | 9/1989 | Smith-Lewis | 436/531 |
| 4,891,324 | 1/1990 | Pease et al. | 436/528 |
| 4,900,685 | 2/1990 | Smith, III | 436/519 |
| 5,043,289 | 8/1991 | Serres | 436/534 |

FOREIGN PATENT DOCUMENTS 0250700  1/1988  European Pat. Off. .

OTHER PUBLICATIONS

Encyclopedia of Chemical Technology, "Diuretics to Emulsions", vol. 8, pp. 159-168.
Encyclopedia of Chemical Technology, "Peroxides and Peroxy Compounds, Inorganic to Piping Systems" vol. 17, pp. 838-843.
I. Khoury et al., *J. Polymer Sci.: Polymer Letters Ed.*, vol. 19, pp. 395-400 (1981).
C. Hsing et al., *J. Polymer Sci.: Polymer Chemistry Ed.*, vol. 21, pp. 457-466 (1983).
A. Pron et al., *J. Chem. Phys.*, vol. 83, pp. 5923-5927 (1985).
S. Armes et al., *J. Colloidal and Interface Sci.*, vol. 118, No. 2, pp. 410-416 (1987).
T. Chao et al., *J. Polymer Sci.: Part A.: Polymer Chemistry*, vol. 26, pp. 743-753 (1988).

*Primary Examiner*—Jill A. Johnston
*Attorney, Agent, or Firm*—Gregory W. Steele; Thomas M. Breininger; Lawrence S. Pope

[57] ABSTRACT

An indicator reagent, assay method and test kit for determining the presence or amount of an analyte in a test sample, in which the indicator reagent is formed by attaching an organic polymer latex particle, preferably a colored particle, to a specific binding member. The specific binding member can be adsorbed onto or covalently bound to the organic polymer latex particles. The organic polymer latex particles are readily detected by direct visual observation or can be detected and/or measured by appropriate instrumentation.

40 Claims, 2 Drawing Sheets

INDICATOR REAGENTS, DIAGNOSTIC ASSAYS AND TEST KITS EMPLOYING ORGANIC POLYMER LATEX PARTICLES

BACKGROUND OF THE INVENTION

1. Field of the Invention

The invention relates generally to the field of indicator reagents and their use in diagnostic assays. More particularly, the present invention relates to the use of organic polymer latex particles as the label components for such indicator reagents, which are especially advantageous in immunoassays.

2. Description of Related Art

Various analytical procedures are commonly used in diagnostic assays to determine the presence and/or amount of substances of interest or clinical significance in test samples, such as body fluids. These clinically significant or interesting substances are commonly referred to as analytes. Diagnostic assays have become an indispensable means for detecting analytes in test samples by using the mutual reaction between the analyte and a specific binding member, as typified by the immunoreaction between an antigen and the antibody to that antigen.

In detecting immunoreactions, use has been made of tags or labels composed of a traceable substance that is attached to a specific binding member, such as an antibody, which in turn binds to the analyte. The detection of the labeled antibody/analyte complex, or of the labeled antibody which remains unbound, is used to indicate the presence or amount of the analyte in the test sample.

Two commonly used immunoreaction techniques are the radioimmunoassay (RIA) and the enzyme immunoassay (EIA), both of which employ a labeled specific binding member, i.e., indicator reagent. The RIA uses a radioactive isotope as the traceable substance attached to a specific binding member. Because the radioactive isotope can be detected in very small amounts, it can be used to detect or quantitate small amounts of analyte. There are, however, a number of substantial drawbacks associated with the RIA. These drawbacks include the special facilities and extreme caution that are required in handling radioactive materials, the high costs of such reagents and their unique disposal requirements.

The EIA uses an enzyme as the label attached to a specific binding member, and enzymatic activity is used to detect the immunoreaction. While the EIA does not have the same disadvantages as the RIA, many EIA techniques require the addition of substrate materials to elicit the detectable enzyme reaction. In addition, enzymes are temperature sensitive and generally have decreased stability at elevated temperatures such as 45° C. shipping temperatures.

More recently, assay techniques using metallic sol particles as labels have been developed. In these techniques, a metal (e.g., gold, silver, platinum), a metal compound, or a nonmetallic substance coated with a metal or a metal compound is used to form an aqueous dispersion of particles. The specific binding member to be labeled is coated onto the metal sol particles by adsorption. The metal sol particles have the advantage of producing a signal that is visually detectable as well as measurable by an instrument, but despite their utility, the inorganic particles have several disadvantages. The metallic particles have a limited color intensity, and therefore, increased amounts of such labels are needed in an assay for ease of detection. In addition, the surfaces of inorganic metallic colloid particles, such as gold, do not readily accept the covalent attachment of specific binding members. Thus, during use in a binding assay, care must be taken so that the adsorbed specific binding members are not removed from the inorganic particles through the combination of displacement by other proteins or surface active agents and the shear forces which accompany washing.

Particles used as labels in immunoassay reagents have also been formed from dye polymers. In this group, dye molecules, i.e., chromogenic monomers, are polymerized to form a colored polymer particle. The dye particles can then be linked to a specific binding member for use in the assay. Examples of such dyes include Congo red, Trypan blue and Lissamine blue.

SUMMARY OF THE INVENTION

The present invention involves indicator reagents, assay methods and test kits for determining the presence and/or amount of an analyte in a test sample. The indicator reagent comprises a label, which is an organic polymer latex particle, comprising a plurality of non-chromophoric monomers, directly or indirectly attached to a specific binding member. The assay method involves contacting the test sample to a capture reagent and the indicator reagent, allowing the indicator reagent to bind to the analyte in the test sample or to the capture reagent, detecting the indicator reagent visually or instrumentally and determining therefrom the presence and/or amount of analyte in the test sample. The test kit contains the indicator reagent and other reagents used in the assay. Preferably, the organic polymer latex particle is a visually detectable colored particle and can include polymers such as poly(pyrrole), polyacetylene, polyphenylene, poly(aniline), poly(thiophene), poly(naphthalene), poly(thiophenol), poly(p-phenylene diethynyl) and derivatives thereof.

DETAILED DESCRIPTION OF THE INVENTION

Figure 1:
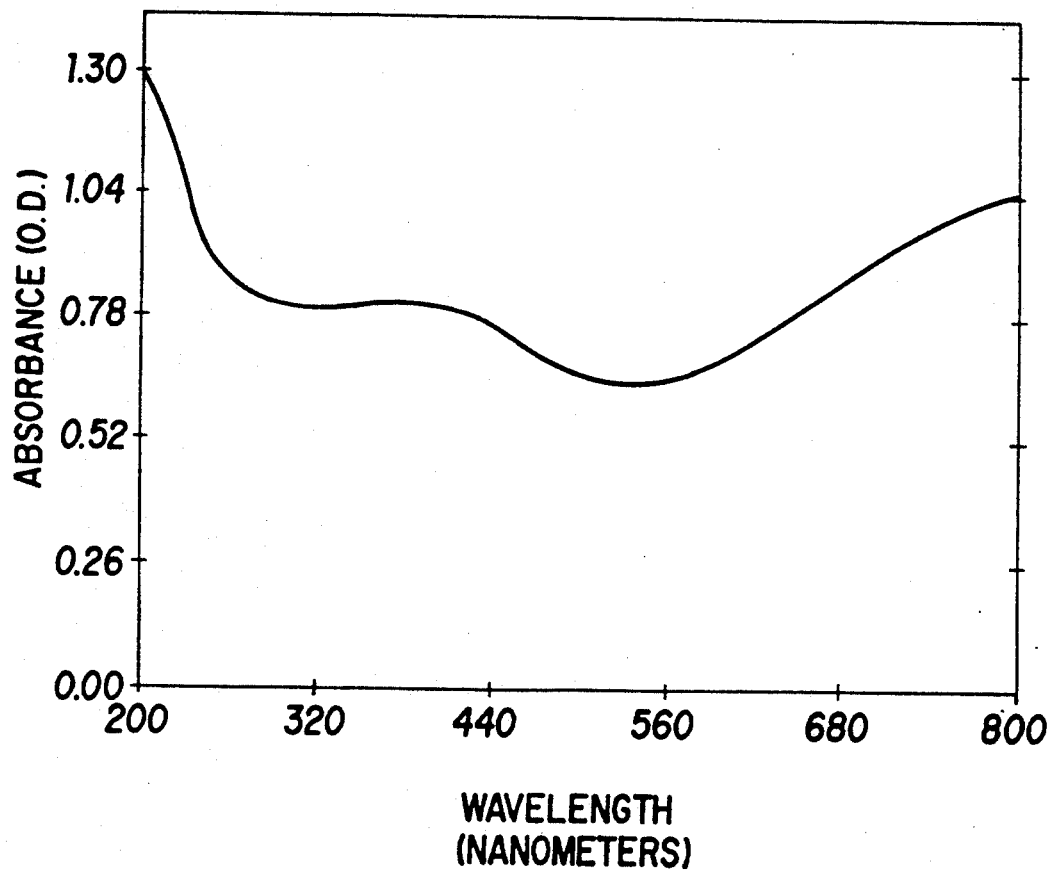
FIG. 1 illustrates the absorption spectra of poly(pyrrole) latex particles, useful in the present invention, at wavelengths of from 200 to 800 nanometers.

As previously stated, the present invention involves an indicator reagent, an assay method and a test kit for determining the presence and/or amount of analyte in a test sample, wherein the indicator reagent comprises an organic polymer latex particle directly or indirectly attached to a specific binding member. In a preferred embodiment of the invention, a substantially colorless organic monomer is polymerized to form a colored organic polymer colloid, and a specific binding member, e.g., antibody, can then be directly or indirectly attached to the colored polymer particle. For example, the specific binding member can be adsorbed onto the particle, or the particle can be functionally adapted so that a specific binding member can be covalently attached to the particle.

Before proceeding further with the description of the various embodiments of the present invention, a number of terms will be defined. A variety of assay techniques in which the indicator reagent of the present invention can be used are also described.

I DEFINITIONS

A "specific binding member", as used herein, is a member of a specific binding pair, i.e., two different molecules where one of the molecules through chemical or physical means specifically binds to the second molecule. In addition to antigen and antibody-specific binding pairs, other specific binding pairs include biotin and avidin, carbohydrates and lectins, complementary nucleotide sequences (including probe and capture nucleic acid sequences used in DNA hybridization assays to detect a target nucleic acid sequence), complementary peptide sequences, effector and receptor molecules, enzyme cofactors and enzymes, enzyme inhibitors and enzymes, and the like. Furthermore, specific binding pairs can include members that are analogs of the original specific binding member. For example, a derivative or fragment of the analyte, i.e., an analyte-analog, can be used so long as it has at least one epitope in common with the analyte. Immunoreactive specific binding members include antigens, haptens, antibodies, and complexes thereof including those formed by recombinant DNA methods or peptide synthesis.

"Analyte", as used herein, is the substance to be detected in the test sample using the present invention. The analyte can be any substance for which there exists a naturally occurring specific binding member (e.g., an antibody) or for which a specific binding member can be prepared, and the analyte can bind to one or more specific binding members in an assay. "Analyte" also includes any antigenic substances, haptens, antibodies, and combinations thereof. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances.

"Indicator reagent", as used herein, comprises a detectable label directly or indirectly attached to a specific binding member. The detectable label of the present invention is an organic polymer latex particle.

"Capture reagent", as used herein, is a specific binding member capable of binding the analyte or indicator reagent and which can be directly or indirectly attached to a substantially solid material. The solid phase:capture reagent complex can be used to separate the bound and unbound components of the assay.

"Ancillary specific binding member", as used herein, is a specific binding member used in addition to the specific binding members of the capture reagent and the indicator reagent and becomes a part of the final binding complex. One or more ancillary specific binding members can be used in an assay. For example, an ancillary specific binding member can be used in an assay where the indicator reagent is capable of binding the ancillary specific binding member which is in turn capable of binding the analyte.

II. REAGENTS AND MATERIALS

Typically, binding assays use an indicator reagent to detect the presence or amount of analyte in a test sample and a solid phase:capture reagent to separate the analyte from the test sample for ease of observation. Optional materials can be present depending upon the desired assay method, and the assay method itself can be varied, for example so as not to include a solid phase such as in a homogeneous immunoassay.

a) Indicator Reagent

In the present invention, the indicator reagent comprises an organic polymer latex particle, as the detectable label, directly or indirectly attached to a specific binding member. A variety of different indicator reagents can be formed by varying either the organic polymer latex particle or the specific binding member. For example, the indicator reagents of the present invention can include monoclonal antibodies affixed to black poly(pyrrole) latex particles or synthetic peptide sequences affixed to violet poly(aniline) latex particles. In general, the indicator reagent is detected or measured after it is captured by a complementary specific binding member, but the unbound indicator reagent can also be measured to determine the result of an assay.

In addition to being either an antigen or an antibody member of an immunoreactive specific binding pair, the specific binding member of the indicator reagent can be a member of any specific binding pair. An immunoreactive specific binding member can be an antibody, antigen, or antibody/antigen complex that is capable of binding either to the analyte as in a sandwich assay, to the capture reagent as in a competitive assay, or to an ancillary specific binding member as in an indirect assay. If an antibody is used, it can be a monoclonal antibody, polyclonal antibody, antibody fragment, recombinant antibody, a mixture thereof, or a mixture of an antibody and other specific binding members. The details of the preparation of such antibodies and their suitability for use as specific binding members are well known to those skilled in the art.

b) Capture Reagent

The capture reagent of the present invention can be a specific binding member, specific either for the analyte as in a sandwich assay, for the indicator reagent and analyte as in a competitive assay, or for an ancillary specific binding member which itself is specific for the analyte as in an indirect assay. Thus, the specific binding member can be any molecule capable of specifically binding with another, just as in the indicator reagent specific binding members. In a solid phase assay, the capture reagent is attached to a solid phase material. The solid phase enables the analyte and other reagents which bind to the capture reagent to be separated from the test solution. Typically, the conjugation of the specific binding member and the solid phase material is substantially irreversible and can include covalent mechanisms.

An assay device of the present invention can have many configurations, several of which are dependent upon the material chosen for the solid phase. Frequently, the solid phase material is any suitable chromatographic, bibulous, porous or capillary material. In the present invention, the solid phase material can include a fiberglass, cellulose or nylon pad for use in a flow-through assay device having one or more layers containing one or more of the assay reagents; a dipstick for a dip and read assay; a test strip for chromatographic (e.g., paper or glass fiber) or thin layer chromatographic (e.g., nitrocellulose) techniques in which one or all of the reagents are contained in separate zones of a single strip of solid phase material; or an absorbent material well known to those skilled in the art. The solid phase material can also include, without limitation, polyacrylamide beads, polystyrene beads or tubes, magnetic beads, a microtitre plate or a glass or plastic test tube.

Natural, synthetic or naturally occurring materials that are synthetically modified, can be used as a solid phase material including polysaccharides, e.g., cellulose materials such as paper and cellulose derivatives such as cellulose acetate and nitrocellulose; silica; silicon particles; inorganic materials such as deactivated alumina, or other inorganic finely divided material uniformly dispersed in a porous polymer matrix, with polymers such as vinyl chloride, vinyl chloride polymer with propylene, and vinyl chloride polymer with vinyl acetate; cloth, both naturally occurring (e.g., cotton) and synthetic (e.g., nylon); porous gels such as silica gel, agarose, dextran, and gelatin; polymeric films such as polyacrylates; protein binding membranes; and the like. The solid phase material should have reasonable strength or strength can be provided by means of a support, and it should not interfere with the production of a detectable signal.

The capture reagent of the present invention, however, is not limited to a specific binding member bound to a solid phase material. In an agglutination assay, the specific binding member of the capture reagent can be bound to a soluble carrier material such as bovine serum albumin.

c) Ancillary Materials

Optionally, the specific binding member of the capture reagent can be affixed to particles, e.g., microparticles. These microparticles can serve as the solid phase material and be retained in a column, suspended in a mixture of soluble reagents and test sample, or retained and immobilized by another solid phase base material. By "retained and immobilized" is meant that the microparticles, associated with the solid phase base material, are not capable of substantial movement to positions elsewhere within that material. The microparticles can be selected by one skilled in the art from any suitable type of particulate material including those composed of polystyrene, polymethylacrylate, polypropylene, polytetrafluoroethylene, polyacrylonitrile, polycarbonate or similar materials. The size of the microparticles is not critical, although it is preferred that the average diameter be smaller than the average pore size of the solid phase base material if such is used. An assay device using microparticles and a solid phase base material is disclosed in copending Abbott U.S. patent application Ser. No. 831,013 commonly assigned herewith.

The present invention further provides kits of reagents and other components for carrying out the assay methods of the invention. For example, a kit according to the present invention can comprise the indicator reagent and any other reagents needed to complete the desired assay technique; other components such as buffers, stabilizers and bacteria inhibiting agents can also be present.

III. DIAGNOSTIC ASSAYS

The organic polymer labels of the present invention can be used in a variety of immunoassay formats. The present invention, however, is not limited to immunoassays. In general, any assay configuration using specific binding members and a detectable label, such as the organic polymer latex particles of the present invention, can be performed.

Binding assays are generally categorized into one of two major classes, homogeneous and heterogeneous assays. In a homogeneous assay, the reaction components or reagents are in the test solution and are not separated prior to the detection of the signal produced by the indicator reagent. In a heterogeneous assay, either a solid phase material is used which allows the separation of bound from unbound reaction components, or a reagent of the initial solution is caused to precipitate and is subsequently removed from the test solution. The indicator reagent of the present invention is detectable in both its bound and unbound forms and can be used in both homogeneous and heterogeneous assays. These assays may be further divided into sandwich and competitive assays, and variations thereof.

The indicator reagent of the present invention is applicable to various types of binding assays. Schematic representations of examples of several such types of assays for antigen and antibody analytes follow. It will be appreciated, however, that one skilled in the art can conceive of many other types of assays, including assays for analytes other than antigens or antibodies, to which the present inventive concepts can be applied.

Heterogeneous Assays

1. Direct Assay

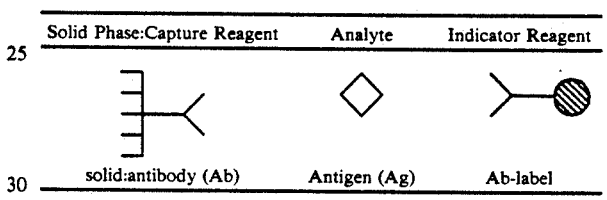

The specific binding member of the indicator reagent may or may not be the same as the specific binding member of the capture reagent. Antigen and antibody analytes are determinable using the foregoing reaction scheme. Variations on the reaction scheme include the following, without limitation:

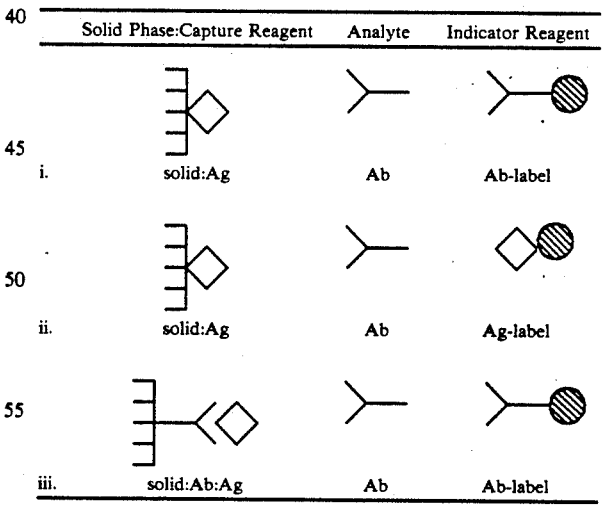

2. Indirect Assay

In this group of assays, an additional specific binding member is used together with those of the indicator and capture reagents to form the detectable binding complex. For example, an ancillary specific binding member can be used where the indicator reagent specifically binds with the ancillary specific binding member which in turn binds to the analyte.

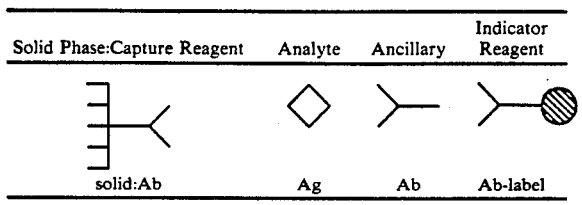

It is also desirable, in some cases, to capture the analyte directly on the solid phase, as follows:

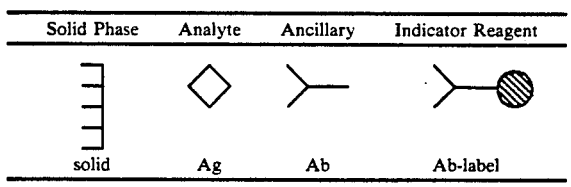

Alternatively, the sandwich complex can be preformed in a homogeneous mixture of capture reagent, analyte and indicator reagent and then separated from the mixture for detection of bound indicator reagent. Such an assay can be performed using a capture reagent that is conjugated to a first charged substance and then separating the reaction complex from the reaction mixture by contacting a solid material which is oppositely charged with respect to the first charged substance. Such an assay method is disclosed in copending Abbott U.S. patent application Ser. No. 150,278 commonly assigned herewith.

3. Competitive Assay

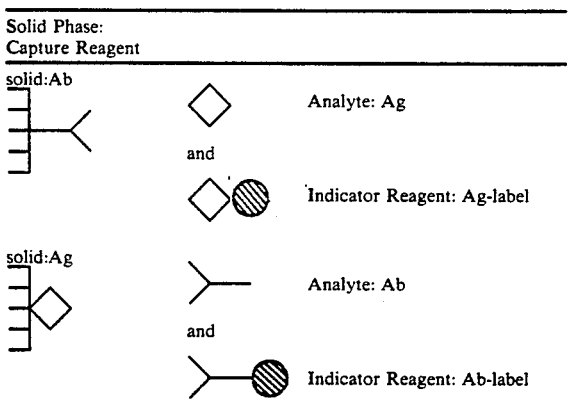

Both the analyte in the test sample and the specific binding member of the indicator reagent are capable of binding to the specific binding member of the capture reagent. The amount of indicator reagent so bound reflects the amount of analyte in the test sample. Ancillary specific binding members can also be used in competitive assays. Generalized examples describing sandwich and competitive assays using the indicator reagent of the present invention are set forth below. Detailed discussions of preferred assay procedures are performed using the indicator reagent of the invention are set forth in the Examples.

In a solid phase sandwich assay, a solid phase is used which includes a capture reagent, i.e., specific binding member which has been bound to a solid support. If the capture reagent is an immunoreactant it can be an antibody, antigen, or complex thereof, specific for the analyte of interest, and if an antibody is used, it can be a monoclonal or polyclonal antibody, an antibody fragment, or a recombinant antibody, as well as a mixture thereof, or a mixture of an antibody and other specific binding members. The capture reagent is contacted with a test sample, suspected of containing the analyte, and an indicator reagent comprising a second specific binding member that has been labeled, for example, an antibody labeled with an organic polymer latex particle. The reagents can be mixed simultaneously or added sequentially, either singly or in combination. A binding reaction results in the formation of a capture reagent-/analyte/indicator reagent complex immobilized upon a solid phase material. The assay can also comprise the step of separating the resultant complex from the excess reagents and test sample. The complex retained on the solid phase material is detected by examining the solid phase for the indicator reagent. If analyte is present in the sample, then label will be present on the solid phase material. The amount of label on the solid phase is a function of the amount of analyte in the sample.

The method of the present invention can be carried out using any of the sandwich assay formats, including the forward, reverse and simultaneous techniques. Typically, a forward assay involves the contact of the test sample to the capture reagent followed by a certain incubation period which is in turn followed by the addition of the indicator reagent. A reverse assay involves the addition of the indicator reagent to the test sample followed by the addition of the capture reagent after a certain incubation period. A simultaneous assay involves a single incubation step as the capture reagent and indicator reagent are both contacted to the test sample at the same time.

In addition, the present invention can be used in an indirect sandwich assay with the formation of a complex of capture reagent/analyte/analyte-specific binding member/indicator reagent. In this case, the additional analyte-specific binding member is the ancillary specific binding member.

The present invention also can be used in a competitive assay. In a solid phase competitive configuration, the solid phase again includes a capture reagent which has been affixed to a solid support and which is contacted with both test sample and an indicator reagent. The indicator reagent, however, is formed from an analyte or analyte-analog which has been labeled with an organic polymer latex particle. A binding reaction occurs and results in the formation of complexes of (1) immobilized capture reagent/analyte complex and (2) immobilized capture reagent/indicator reagent complex. In the competitive assay, the amount of label on the solid phase is inversely related to the amount of analyte in the sample. Thus, a positive test sample will generate a decrease in signal.

For example, in a theophylline assay, an anti-theophylline antibody (either monoclonal or polyclonal capture reagent) can be coated on a solid support to form the solid phase. A competition for binding to that antibody can be established between an indicator reagent of organic polymer latex particle labeled theophylline and the unlabeled theophylline of the test sample. The immunoreaction results in an immobilized capture reagent/indicator reagent complex if theophylline, or a threshold amount of theophylline, is not present in the test sample. Increased theophylline levels in the test sample will result in decreased indicator reagent associated with the solid phase.

Homogeneous Assays

Homogeneous assays do not require the separation of the test solution and the indicator reagent prior to observation of the indicator reagent. This broad classification includes many formats such as those described below as well as others apparent to one skilled in the art using the indicator reagents of the present invention.

A major category of homogeneous assays are the agglutination assays which can also be performed using the indicator reagents of the present invention. Agglutination reactions and their procedures are generally well known in the art. A typical agglutination reaction consists of the clumping together, in suspension, of analyte in the presence of an analyte-specific binding member. This clumping or agglutination of reaction components is monitored to determine the presence or amount of the analyte sought to be detected. The agglutination reaction can be monitored by labeling a reaction component, e.g., a specific binding member, with the organic polymer latex particles and detecting the signal associated with either the agglutinated or the unagglutinated reagents. Detection can be achieved visually by observing the clumping of the reaction medium, by the settling or pelleting of the indicator reagent in a gravitational field, by changes in light scattering, or by changes in the spectral properties of the indicator reagent.

1. Direct Assay

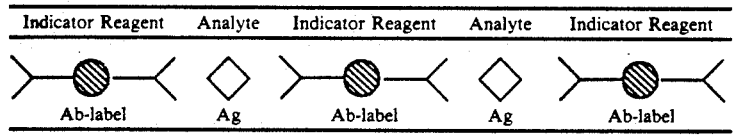

In a direct agglutination assay, the indicator reagent again comprises an analyte-specific binding member directly or indirectly attached to an organic polymer latex particle label. In the presence of a polyvalent analyte, two or more labeled specific binding members can bind to the analyte, thereby causing the indicator reagent and analyte to aggregate. An increase in the aggregation can indicate an increase in the amount of analyte present in the test sample.

2. Indirect/Competitive Assay

An indirect agglutination assay can be constructed using an ancillary binding member that competes with the analyte for binding to the indicator reagent. Such an assay configuration is especially useful for the analysis of a monovalent analyte. In this assay, more than one ancillary binding member is attached to a carrier material and is contacted to the indicator reagent and test sample. If the analyte is absent, or below a threshold level, then agglutination occurs due to the binding of more than one indicator reagent to the carrier material. If the analyte is present in the test sample, then the analyte competitively binds to the indicator reagent, thereby blocking the indicator reagent's binding to the carrier, and the presence of the analyte is indicated by a decrease in agglutination of the indicator reagent.

IV. ORGANIC POLYMER LATEX PARTICLES

The polymer particles of the present invention are made by polymerizing a nonchromophoric monomer; nonchromophoric monomer, as used herein, refers to an organic monomer which is neither a pigment or a dye and which has color or absorbance characteristics that make the unpolymerized substance unsuitable for use as a detectable label. The resulting polymer particles absorb light in the visible, ultraviolet or infrared regions at one or more wavelengths at which the monomer does not. The polymer particle's absorbance characteristics are due to the extensively conjugated structure resulting from the polymerization process. Thus, the polymer particle derives its characteristic color or absorbance from its polymeric structure rather than from the color or absorbance of the monomer from which it is made or from the addition of a dye or a pigment, i.e., a chromogen. For example, pure monomeric pyrrole is a substantially nonchromophoric substance, but the poly(pyrrole) latex particle is black due to its extensively conjugated structure and unpaired delocalized electrons (stable radicals). Aniline is a substantially nonchromophoric monomer, but poly(aniline) latex particles can have colors ranging from yellow to violet depending on the level to which the polymer is oxidized during polymerization. "Substantially" nonchromophoric refers to the fact that impurities may be present that impart a color to the monomer, although typically, the pure form of the monomer is transparent or colorless.

The organic polymer latex particles of this invention can be divided into at least six classes. The first class comprises a polymer particle made from a single nonchromophoric monomer material. Such polymer particles include, but are not limited to, particles made of the following: poly(pyrrole); polyacetylene; polyphenylene; poly(aniline); poly(thiophene); poly(naphthalene); poly(thiophenol); their derivatives, such as poly(n-methyl pyrrole), poly(n-benzyl pyrrole), poly(n-phenyl pyrrole) [e.g., poly(1-phenyl 2,5 pyrrolylene)] and poly(p-phenylene diethynyl), i.e., (—C≡C—C$_6$H$_4$C≡C—); and their equivalents.

The second class of polymer particles comprises a composite of both nonchromophoric monomers, which upon polymerization form a colored polymer, and nonchromophoric monomers which upon polymerization generally do not form a colored polymer. Composite particles can be formed by combining one of the above described polymers, or oligomers thereof, with moldable polymer materials such as poly(vinyl chloride), polystyrene and poly(vinyl toluene), as well as hydrophilic polymer materials such as poly(acrylamide) and poly(N-vinyl pyrrolidone), and derivatives thereof. The composite particles of blended materials, may facilitate processing of the particle labels.

The third class includes polymer particles having repeating units of at least two different nonchromophoric monomers. Thus, copolymers can be formed and used as labels according to the present invention. Examples of copolymers include, but are not limited to, poly(pyrrole-co-thiophene) and poly(pyrrole-co-phenylene). The organic monomers include: pyrrole, benzene, toluene, aniline, thiophene, naphthalene, thiophenol and equivalent aromatic monomers; acetylene and equivalent non-aromatic monomers; and derivatives thereof.

The fourth class of polymer particles comprises an organic or inorganic nucleus which can be coated with a polymer made by the polymerization of a plurality of nonchromophoric monomers. For example, a metallic colloidal particle can be coated with the colored organic polymer latex.

The fifth class comprises a polymer particle made of a plurality of nonchromophoric monomers polymerized to form a substantially colorless polymer particle which upon further reaction, with a substance which is not a dye or pigment, will become a colored polymer particle. An example of such a polymer particle is poly(phenylene sulfide), a normally transparent and substantially colorless polymeric material, which becomes blue-green and finally blue-black upon further reaction with arsenic pentafluoride.

The sixth class comprises a polymer particle made of a plurality of nonchromophoric monomers which upon polymerization form a particle having detectable free radicals, but the resulting particle can be colored or substantially colorless. While such colorless particles may not be visually detectable, the stable free radical nature of these particles enables their detection and measurement with an electron paramagnetic resonance spectrometer.

The polymer particles of the present invention can be used to label or tag specific binding members, thereby forming indicator reagents for use in a variety of binding assay techniques. The polymer particles can be used in both homogeneous and heterogeneous assay techniques as described above. Preferably, the particles are used in heterogeneous solid phase assays such as the direct sandwich immunoassay described above. More preferably, the polymer particles are used as labels in solid phase assays which rely upon the direct visual observation of the label to determine the presence or amount of an analyte in a test sample. The present invention can be used not only in the above described binding assay techniques, but can be modified by one skilled in the art for carrying out other heterogeneous and homogeneous specific binding assays without departing from the inventive concepts embodied herein. For example, the organic polymer latex particles of the present invention can also be modified for use as a labeled constituent in histology, nephelometry and histochemistry.

The size of the organic polymer latex particles is not critical and will vary according to the particular assay format or absorbance desired. The optimization of all elements and reagents of the assay, including particle size, can be determined by one skilled in the art with routine testing. A particle size with a range substantially from about 10 nm to about 15 μm can be used in known assay formats. Preferably, a particle size with a range substantially from about 50 nm to about 1.0 μm will be used, and most preferably, a particle size with a range substantially from about 100 nm to about 500 nm will be used.

The organic polymer latex particles of the present invention can be detected by direct visual observation, or they can be measured by an instrument, such as a simple colorimeter, reflectometer or densitometer. In addition, the stable free radical nature of the materials of the present invention also enables detection and measurement of a particle's electron paramagnetic resonance. Detection by appropriate instrumental means will be necessary if the polymer particle label does not absorb light in the visible spectrum. Alternatively, an instrumental means may be required to quantitate the amount of indicator reagent that is present. Preferably, the polymer particle is visually detectable to facilitate its use.

It is relatively easy to covalently attach organic specific binding members to the organic polymer latex particle labels to form the indicator reagent of the present invention. The specific binding member can be attached to the particles either by adsorption, a linking group or a surface-functional group. By covalently attaching the specific binding member to the surface of the label, an increase in surface concentration and stability toward displacement may be achieved. Covalent attachment can be accomplished using carboxylic, amino, aldehyde, bromoacetyl, iodoacetyl, thiol, epoxy and other reactive or linking groups, as well as residual free radicals and radical cations, through which a protein coupling reaction can be accomplished. A surface functional group can be incorporated as a functionalized co-monomer because the surface of the polymer particle can contain a relatively high surface concentration of polar groups. The organic polymer latex particles of the present invention are typically functionalized after synthesis, but in certain cases, such as poly(thiophenol), the particle is capable of direct covalent linking with a protein without the need for further modification.

Preparation of organic polymer latex particles a. Poly(pyrrole) latex particles

Poly(pyrrole) latex particles were prepared according to a modified method described in "Aqueous Dispersions of Electrically Conducting Monodisperse Poly(pyrrole) Particles" (S. P. Armes, et al., Journal of Colloid and Interface Science, 118: 410–416, 1987).

Reagent grade pyrrole (Aldrich Chemical Co., Milwaukee, Wis.) was vacuum distilled (at 53° C., 35 mm Hg) using a six inch unpacked column. Poly(vinyl alcohol) (0.298 g, 88% hydrolyzed, 125,000 mol. wt; Aldrich) and $FeCl_3 \cdot 6H_2O$ (Aldrich) was dissolved in distilled water (100 ml). The solution was transferred to a magnetically stirred round-bottom flask and one milliliter of the distilled pyrrole was added. The solution turned from orange to black in about five seconds. The reaction was allowed to continue, with stirring, at 20° C. for four hours.

The resultant organic polymer latex particles were purified by placing the colloidal suspension in glass centrifuge tubes and centrifuging at $13,000 \times g$ for 35 to 45 minutes. The supernatant was replaced with distilled water, and the particles were redispersed with gentle agitation. This process was then repeated.

The percentage solids content of the suspension of organic polymer latex particles was determined by weighing a wet sample into a preweighed glass vial and placing the vial in an oven set at 110° C. for four hours. The vial containing the dried material was reweighed and the solids content was calculated based on the weight loss on drying. Solids analysis of the unpurified reaction mixture immediately after synthesis, correcting for initiator and stabilizer, indicated a 95% conversion of monomer to polymer.

A dilute aqueous suspension was measured by photon correlation spectroscopy to determine the particle diameter. Individual lots were monodispersed with particles typically having an average diameter of 190 nm.

Figure 2:
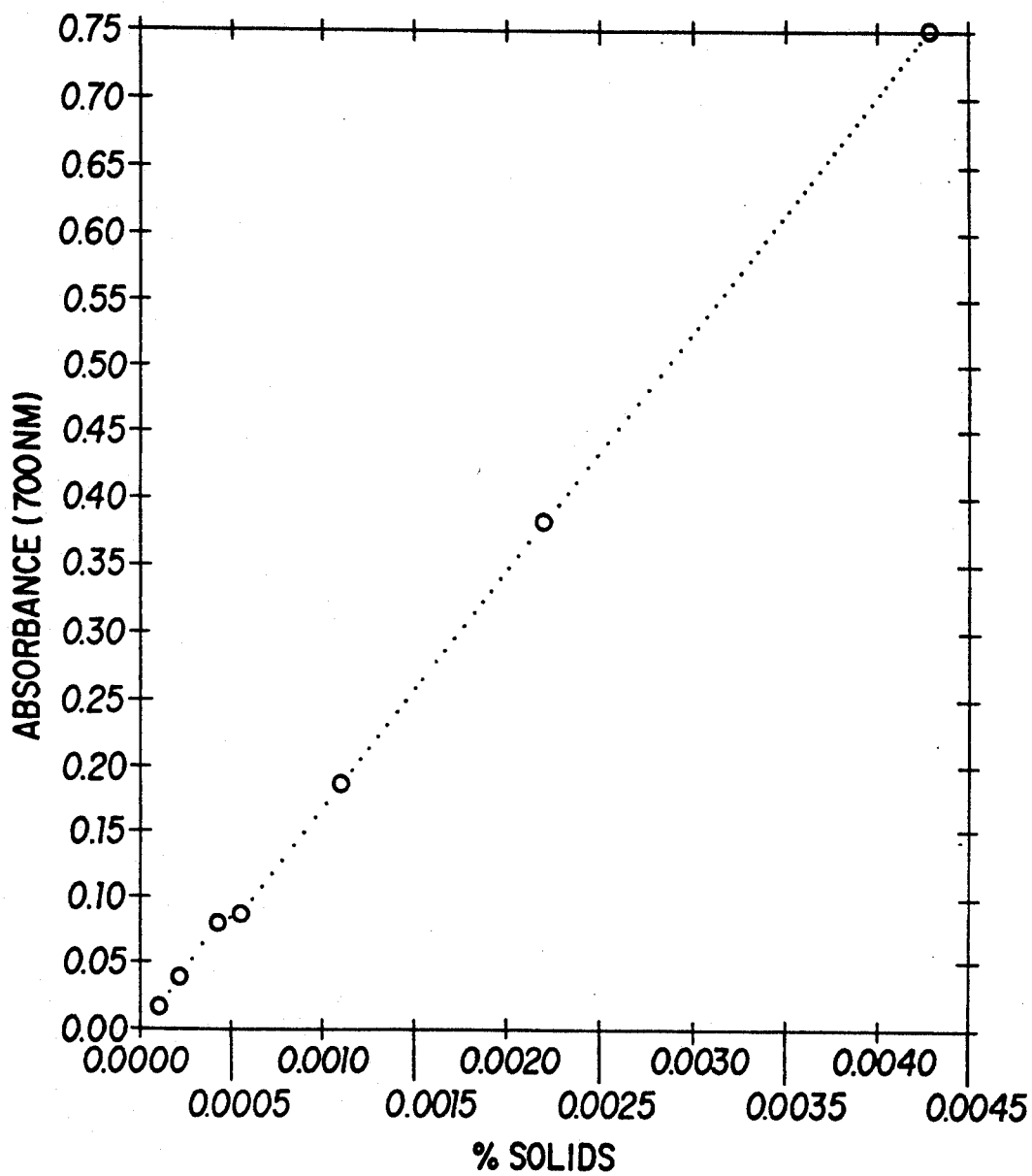
FIG. 2 illustrates the absorbance of poly(pyrrole) latex particles, useful in the present invention, at a wavelength of 700 nanometers for particle preparations having various percent solids.

The absorption spectra of the material at 0.00216% solids is shown in FIG. 1. High absorption was found in the ultraviolet and at long wavelengths. The visible spectra was essentially flat with only a slight dip at about 510 nanometers. The absorbance at 700 nanometers vs % solids was a straight line (FIG. 2). At 0.001% solids an absorbance of about 0.175 AU was found. The high absorbance at the broad range of wavelengths indicated that the organic polymer latex particle label can be detected or quantitated at any visible wavelength rather than a particular peak wavelength.

b. Preparation of bromoacetylated poly(pyrrole) latex

Unpurified poly(pyrrole) latex (200 ml, prepared substantially in accordance with the method described above) was centrifuged and washed with an equal volume of distilled water. The preparation was then solvent exchanged into N-methyl-2-pyrrolidinone and resulted in a 57 g sample of suspension at 1.9% solids. Sixty-four milliliters of 1,4-dioxane was added to the suspension to remove the residual water, and the water/dioxane azeotrope was removed on a rotary evaporator under reduced pressure at 40° C.

The dried poly(pyrrole) suspension [1.09 g poly(pyrrole)=0.0162 equivalents] was placed on a magnetic stirrer in an ice bath. Bromoacetyl bromide (3.2 ml=4.92 g=0.0243 equivalents) was added by drops to the chilled suspension. After 20 minutes, triethylamine (3.4 ml=2.46 g=0.0243 equivalents) was added, by drops, and the flask was then removed from the ice bath. The reaction was allowed to proceed overnight. A white precipitate of triethylamine hydrobromide was filtered from the suspension, and the resultant organic polymer latex particles were washed with two equal volumes of dioxane. Samples of the suspension were dried in an oven at 110° C. for four hours. Spectroscopic evidence (mass spectroscopy) indicated the bromoacetyl surface functionality had been formed. Mass spectroscopy exhibited polymeric fragments having characteristic doublets due to the 79 and 81 isotopes of bromine. Elemental analysis for bromine indicated a 30% conversion to the bromoacetyl derivative.

c. Poly(aniline) latex particles

Poly(aniline) latex particles were formed using a modification of a technique used to prepare precipitated poly(aniline) (J. Chem. Soc. Faraday Trans. 1, 82: 2385-2400; 1986). Poly(vinyl alcohol) (0.298 g; 88% hydrolyzed) was dissolved in HCl (400 ml, 1 N). To this solution was added potassium persulfate (5.93 g, 0.0219 mol). The mixture was transferred to a round-bottom flask equipped with a magnetic stirrer, and with stirring, aniline was added (1.022 g). The mixture became darkly colored green approximately 15 minutes after adding the aniline. Organic polymer latex particles were formed with the change in color depending on the pH and the degree of oxidation. Aggregates were separated from the colloid material by slow speed centrifugation.

d Polyphenylene latex particles

A round bottom flask (250 ml) was fitted with a magnetic stirrer, a heating mantle, a condenser, and an inlet and outlet for helium. In the flask, under a stream of helium, poly(vinyl alcohol) (0.31 g, 88% hydrolyzed, 125,000 mw) was dissolved in distilled water (100 ml) to form a solution. Iron III chloride hexahydrate (13.5 g; 0.050 mole) was dissolved in this solution. Benzene (1 ml) was added to the solution with stirring, and the temperature was raised to 70°-75° C. After ten minutes at that temperature, an additional one milliliter of benzene was added, and the solution was stirred and heated for a total of 70 minutes. During that time, the solution turned from a clear yellow to a turbid and rust-colored polyphenylene colloidal suspension, and the evolution of HCl gas was evident in the helium outlet stream. The suspension of organic polymer latex particles was cooled, and aliquots were centrifuged and washed with distilled water. The polyphenylene particle size ranged from 0.7-3.0 microns as measured by light microscopy.

EXAMPLES

The following Examples illustrate how to make the novel materials of the present invention and how to perform assay procedures using those materials. The Examples, however, are intended only to be illustrative, and are not to be construed as placing limitations upon the scope of the invention, which scope is defined solely by the appended claims.

EXAMPLE 1

Hepatitis B surface antigen immunoassay a. Preparation of an anti-biotin antibody/poly(pyrrole) indicator reagent A ten milliliter volume of poly(pyrrole) latex particles (0.1% in distilled water, prepared substantially in accordance with the protocol described above) was placed in a vial. Tris(hydroxymethyl)aminomethane buffer (Tris, one ml, 100 mM, pH 7.5) was added with stirring, followed by 1% bovine serum albumin (BSA, 50 μl in distilled water) and rabbit anti-biotin antibody (500 μl, 1 mg/ml). The mixture was incubated at room temperature for one hour, after which the organic polymer latex particles were separated from the supernatant liquid by centrifugation. The particles were resuspended in Tris buffer containing BSA.

b. Hepatitis B surface antigen (HBsAg) indirect sandwich assay

A capture reagent was prepared by immobilizing anti-HBsAg antibody on a nitrocellulose test strip. The strip was then contacted to a sample consisting of 120 μl of human plasma containing a defined amount of HBsAg. The sample was drawn up the strip by capillary action, past the immobilized capture antibody, so that HBsAg in the sample would be captured by the immobilized anti-HBsAg antibody. In a similar manner, biotinylated anti-HBsAg antibody (ancillary specific binding member, 10 μl of a 2 μg/ml solution) was contacted to the strip and was bound to the immobilized HBsAg analyte. This was followed by contacting the strip with the indicator reagent of Example 1.a (15 μl), the anti-biotin portion of which bound to the ancillary specific binding member.

In samples containing a threshold amount of HBsAg, the antigen reacted with the capture reagent and was immobilized on the nitrocellulose test strip. The biotinylated anti-HBsAg antibody then reacted with the antigen, and the indicator reagent completed the immunocomplex by binding to the biotinylated anti-HBsAg antibody. The immobilized indicator reagent was detectable as a dark area on the strip, and the intensity of the color was directly related to the quantity of HBsAg in the sample. Table 1 presents the intensity of the color obtained for various concentrations of HBsAg analyte. The results demonstrate that as the analyte concentration increased, the indicator reagent and thus the detectable color also increased on the test strip.

TABLE 1

| HBsAg indirect sandwich assay | |
|---|---|
| HBsAg concentration (ng/ml) | Color intensity (relative densitometer units) |
| 0 | 0 |
| 5 | 20 |
| 10 | 50 |
| 20 | 120 |
| 100 | 270 |

EXAMPLE 2

AIDS antibody immunoassay a. Preparation of an HIV-p24 antigen/poly(pyrrole) indicator reagent One milliliter of poly(pyrrole) latex particles (0.1% in distilled water, prepared substantially in accordance with the protocol described above) was placed in a vial. Borate buffer (100 μl, 100 mM, pH 8.0) was added with stirring, followed by HIV-p24 antigen (the major core protein of HIV, 20 μl of 0.75 mg/ml). The mixture was incubated at room temperature for one hour, after which BSA was added to the resultant indicator reagent.

b. HIV-p24 antibody sandwich assay

A capture reagent was prepared by immobilizing HIV-p24 antigen on a nitrocellulose filter strip. The test sample, human plasma containing various dilutions of antibody specific to HIV-p24, was mixed with an equal volume of the HIV-p24 antigen/poly(pyrrole) indicator reagent of Example 2.a. Forty microliters of the indicator reagent/test sample mixture was then applied to the nitrocellulose strip, and the fluid was drawn up the strip past the immobilized antigen. In samples containing antibody to HIV-p24, that antibody reacted with the antigen on the solid phase as well as with the antigen of the indicator reagent to form an antigen/antibody/antigen sandwich immunocomplex on the nitrocellulose test strip. The immobilized indicator reagent was detectable as a dark area on the strip, and the intensity of the color was directly related to the quantity of anti-HIV-p24 antibody in the test sample, as demonstrated by the results presented in Table 2. The results demonstrate that as the analyte concentration increased, the indicator reagent and thus the detectable color increased on the test strip.

TABLE 2

| HIV-p24 sandwich assay | |
|---|---|
| anti-HIV-p24 antibody dilution | Color intensity (relative densitometer units) |
| 0 | 0 |
| 1/1000 | 8.8 |
| 1/100 | 40.4 |
| 1/10 | 62.6 |

The following examples present the use of the indicator reagent in a solid phase flowthrough immunoassay method, as demonstrated with both nitrocellulose and glass fiber solid phase materials.

EXAMPLE 3

Nitrocellulose flow-through assay for digoxin a. Preparation of an anti-digoxin antibody/poly(pyrrole) indicator reagent The indicator reagent was made of affinity purified sheep anti-digoxin antibody (75 μg/ml in 75 mM PO$_4$ and 300 mM NaCl at pH 6.8) adsorbed to black poly(-pyrrole) latex particles (2.3% solids, 213 nm diameter, prepared substantially in accordance with the protocol described above) by incubating in bis-Tris (2-hydroxyethyl-Tris, 25 mM at pH 6.5) for one hour at room temperature. This was followed by an overnight incubation at 4° C. while rotating. Free antibody was removed by centrifugation of the resultant indicator reagent. The surfaces of the organic polymer latex particles were blocked with 0.5% BSA and 0.02% polyoxyethylenesorbitan monolaurate (Tween-20).

b. Preparation of a nitrocellulose solid phase

A nitrocellulose filter material, with five micron pores, was treated with fifty microliters of 10% digoxin-BSA (0.005% Tween-20) and was left to stand for 15 minutes at room temperature. The digoxin-BSA was prepared substantially in accordance with the method described in Butler V. P. and Chen J. P., Proc. Natl. Acad. Sci. USA, 57:71–78 (1967). Fifty microliters of digoxin-BSA stock solutions of 20, 30 and 40 μg/ml were used to place approximately 1.0, 1.5 and 2.0 micrograms of digoxin-BSA on the solid phase. A blocking agent (50 μl of 10% BSA, 0.05% Tween-20) was then added to the solid phase and left to stand for five minutes at room temperature. The nitrocellulose filter material was then rinsed with an assay buffer wash (50 μl; 25 mM bis-Tris, 0.5% BSA, 0.02% Tween-20 and 0.02% NaN$_3$ at pH 6.5)

c. Digoxin competitive immunoassay

A test sample was incubated for ten minutes at 37° C. with the indicator reagent of Example 3.a. The mixture was applied to the treated nitrocellulose pad which was placed over a highly absorbent backing material. The pad was washed, two times, with assay buffer (300 μl). The signal on the pad was then read using a surface reflectance reader.

The anti-digoxin antibody of the indicator reagent bound to the digoxin-BSA on the nitrocellulose and formed a colored surface with a low reflectance. When the test sample contained digoxin, the antibody sites were blocked and less indicator reagent bound to the nitrocellulose. This resulted in an increased reflectance when there were increased amounts of digoxin in the test sample.

The assay results are presented in Table 3 which compares analyte concentrations and capture reagent concentrations with the measured reflectance in relative units; two samples at each concentration of analyte were performed, and the mean and standard deviation were determined. The results demonstrated that as the amount of digoxin in the test sample increased, the amount of indicator reagent bound to the nitrocellulose pad decreased.

TABLE 3

| Reflectance measurements for nitrocellulose pad flow-through assay | | | | | |
|---|---|---|---|---|---|
| | Digoxin (ng/ml) | | | | |
| digoxin-BSA μg | 0.0 | 0.5 | 1.0 | 2.0 | 5.0 |
| 1.00 | 59.3, 58.2 | 65.2, 71.1 | 84.4, 86.5 | 131, 130 | 166, 172 |
| mean ± s.d. | 58.8 ± 0.8 | 68.2 ± 4.0 | 85.5 ± 1.5 | 131 ± 0.7 | 169 ± 4.2 |
| 1.50 | 54.2, 46.1 | 56.7, 57.3 | 73.3, 76.2 | 120, 120 | 166, 167 |
| mean ± s.d. | 50.2 ± 5.7 | 57.0 ± 0.4 | 74.8 ± 2.1 | 120 ± 0.0 | 167 ± 0.7 |
| 2.0 | 38.4, 37.9 | 53.0, 45.4 | 65.3, 64.0 | 112, 114 | 165, 172 |
| mean ± s.d. | 38.2 ± | 49.2 ± | 64.7 ± | 113 ± | 169 ± 4.9 |

TABLE 3-continued

Reflectance measurements for nitrocellulose pad flow-through assay

| digoxin-BSA μg | Digoxin (ng/ml) | | | | |
|---|---|---|---|---|---|
| | 0.0 | 0.5 | 1.0 | 2.0 | 5.0 |
| | | 0.4 | 5.4 | 0.9 | 1.4 |

EXAMPLE 4

Glass fiber flow-through assay for digoxin a. Preparation of a class fiber solid phase A glass fiber filter (Hollingsworth and Voss, West Groton, Mass.) was prepared substantially in accordance with the protocol described in Example 3.b for the nitrocellulose solid phase. Digoxin-BSA stock solutions of 125, 250 and 500 μg/ml were used to place approximately 6.25, 12.5 and 25.0 micrograms of digoxin-BSA on the filter.

b. Digoxin competitive assay

The assay was performed substantially in accordance with the protocol described in Example 3.c. The assay results are presented in Table 4. The results demonstrated that as the amount of digoxin in the test sample increased, the amount of indicator reagent bound to the glass fiber pad decreased.

TABLE 4

Reflectance measurements for glass fiber flow-through assay

| digoxin-BSA μg | Digoxin (ng/ml) | | | | |
|---|---|---|---|---|---|
| | 0.0 | 0.5 | 1.0 | 2.0 | 5.0 |
| 6.25 | 87.5, 83.2 | 86.1, 85.5 | 100, 98.8 | 126, 125 | 161, 163 |
| mean ± s.d. | 85.4 ± 3.0 | 85.8 ± 0.4 | 99.4 ± 0.8 | 126 ± 0.7 | 162 ± 1.4 |
| 12.50 | 78.3, 81.5 | 84.1, 83.0 | 93.8, 94.7 | 130, 123 | 160, 160 |
| mean ± s.d. | 79.9 ± 2.3 | 83.6 ± 0.8 | 94.3 ± 0.6 | 127 ± 4.9 | 160 ± 0.0 |
| 25.00 | 78.4, 73.5 | 80.6, 83.2 | 91.3, 90.0 | 125, 123 | 155, 159 |
| mean ± s.d. | 76.0 ± 3.5 | 81.9 ± 1.8 | 90.7 ± 0.9 | 124 ± 1.4 | 157 ± 2.8 |

The concepts of the present invention are applicable to various types of binding assays. It will be appreciated, however, that one skilled in the art can conceive of other assays, including assays for analytes other than antigens or antibodies, to which the present inventive concepts can be applied. The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as previously described and as set forth in the following claims.

What is claimed is:

1. An indicator reagent, useful for determining the presence or amount of an analyte in a test sample, comprising:

a. an organic polymer latex particle prepared from the polymerization of a plurality of nonchromophoric monomers, said particle selected from the group consisting of poly(pyrrole), polyphenylene, poly(aniline), poly(thiophene), poly(naphthalene), poly(thiophenol), polyacetylene and derivatives thereof, said particle having light absorbance characteristics resulting from a conjugated structure from the polymerization of said monomers wherein said polymer latex particle exhibits increased absorbance in the visible spectrum compared to the absorbance in the visible spectrum of the aggregate of nonchromophoric monomers from which it is prepared, and b. a specific binding member directly or indirectly attached to said particle.

2. The indicator reagent according to claim 1, wherein said organic polymer latex particle is a colored particle.

3. The indicator reagent according to claim 1, wherein said organic polymer latex particle is a composite particle further comprising a polymer material selected from the group consisting of poly(vinyl chloride), polystyrene, poly(vinyl toluene), poly(acrylamide), poly(N-vinyl pyrrolidone) and derivatives thereof.

4. The indicator reagent according to claim 1, wherein said organic polymer latex particle is a copolymer comprising at least two different monomers.

5. The indicator reagent according to claim 4, wherein said monomers are selected from the group consisting of pyrrole, benzene, toluene, aniline, thiophene, naphthalene, thiophenol, acetylene and derivatives thereof.

6. The indicator reagent according to claim 1, wherein the specific binding member is selected from the group consisting of biotin, avidin, carbohydrates, lectins, complementary nucleic acid sequences, non-immunoreactant receptor molecules, complementary members to the non-immunoreactant receptor molecules, enzyme cofactors, enzymes, enzyme inhibitors and immunoreactants.

7. The indicator reagent according to claim 6, wherein said immunoreactant is selected from the group consisting of monoclonal antibody, polyclonal antibody, antibody fragment, recombinant antibody, recombinant protein, hapten, antigen and complexes thereof.

8. The indicator reagent according to claim 1, wherein said specific binding member is attached to said organic polymer latex particle by adsorption.

9. The indicator reagent according to claim 1, wherein said specific binding member is attached to said organic polymer latex particle by a linking group.

10. The indicator reagent according to claim 9, wherein said linking group is selected from the group consisting of carboxylic, amino, aldehyde, bromoacetyl, iodoacetyl, thiol, and epoxy reactive groups, residual free radicals and radical cations.

11. The indicator reagent according to claim 1, wherein said specific binding member of said indicator reagent is specific for a substance selected from the group consisting of the analyte as in a sandwich assay, a capture reagent as in a competitive assay and an ancillary specific binding member as in an indirect assay.

12. The indicator reagent according to claim 1, wherein said organic polymer latex particle becomes a colored particle upon further reaction with at least one additional nonchromophoric substance.

13. The indicator reagent according to claim 1, wherein said organic polymer latex particle is detectable by electron paramagnetic resonance.

14. A method for determining the presence or amount of an analyte in a test sample, comprising:

a. contacting the test sample sequentially or simultaneously with an indicator reagent and a capture reagent, directly or indirectly attached to a specific binding member, said indicator reagent comprising an organic polymer latex particle prepared from the polymerization of a plurality of nonchromophoric monomers, said particle having light absorbance characteristics resulting from a conjugated structure from the polymerization of said monomers wherein said polymer latex particle exhibits increased absorbance in the visible spectrum compared to the absorbance in the visible spectrum of the aggregate of nonchromophoric monomers from which it is prepared; and b. allowing said indicator reagent to bind to the analyte in the test sample or to said capture reagent;

c. detecting said indicator reagent; and d. determining thereby the presence or amount of analyte in the test sample.

15. The method according to claim 14, wherein said organic polymer latex particle is a colored particle.

16. The method according to claim 15, wherein said organic polymer latex particle is selected from the group consisting of poly(pyrrole), polyphenylene, poly(aniline), poly(thiophene), poly(naphthalene), poly(thiophenol), polyacetylene and derivatives thereof.

17. The method according to claim 14, wherein said organic polymer latex particle is a composite particle further comprising a polymer material selected from the group consisting of poly(vinyl chloride), polystyrene, poly(vinyl toluene), poly(acrylamide), poly(N-vinyl pyrrolidone) and derivatives thereof.

18. The method according to claim 14, wherein said organic polymer latex particle is a copolymer comprising at least two different monomers.

19. The method according to claim 18, wherein said monomers are selected from the group consisting of pyrrole, benzene, toluene, aniline, thiophene, naphthalene, thiophenol, acetylene and derivatives thereof.

20. The method according to claim 14, wherein said organic polymer latex particle comprises a particle which is coated with an organic polymer latex selected from the group consisting of poly(pyrrole), polyacetylene, polyphenylene, poly(aniline), poly(thiophene), poly(naphthalene), poly(thiophenol) and derivatives thereof.

21. The indicator reagent according to claim 14, wherein the specific binding member is selected from the group consisting of biotin, avidin, carbohydrates, lectins, complementary nucleic acid sequences, non-immunoreactant receptor molecules, complementary members to the non-immunoreactant receptor molecules, enzyme cofactors, enzymes, enzyme inhibitors and immunoreactants.

22. The method according to claim 21, wherein said immunoreactant is selected from the group consisting of monoclonal antibody, polyclonal antibody, antibody fragment, recombinant antibody, recombinant protein, hapten, antigen and complexes thereof.

23. The method according to claim 14, wherein said specific binding member is attached to said organic polymer latex particle by adsorption.

24. The method according to claim 14, wherein said specific binding member is attached to said organic polymer latex particle by a linking group.

25. The method according to claim 24, wherein said linking group is selected from the group consisting of carboxylic, amino, aldehyde, bromoacetyl, iodoacetyl, thiol, and epoxy reactive groups, residual free radicals and radical cations.

26. The method according to claim 14, wherein said specific binding member of said indicator reagent is specific for a substance selected from the group consisting of the analyte as in a sandwich assay, a capture reagent as in a competitive assay and an ancillary specific binding member as in an indirect assay.

27. The method according to claim 14, wherein said organic polymer latex particle becomes a colored particle upon further reaction with at least one additional nonchromophoric substance.

28. The method according to claim 14, wherein said organic polymer latex particle is detectable by electron paramagnetic resonance.

29. The indicator reagent according to claim 14, wherein said capture reagent is selected from the group consisting of biotin, avidin, carbohydrates, lectins, complementary nucleic acid sequences, non-immunoreactant receptor molecules, complementary members to the non-immunoreactant receptor molecules, enzyme cofactors, enzymes, enzyme inhibitors and immunoreactants.

30. The method according to claim 29, wherein said immunoreactant is selected from the group consisting of monoclonal antibody, polyclonal antibody, antibody fragment, recombinant antibody, recombinant protein, hapten, antigen and complexes thereof.

31. The method according to claim 29, wherein said specific binding member of said capture reagent is specific for a substance selected from the group consisting of the analyte as in a sandwich assay, said indicator reagent as in a competitive assay and an ancillary specific binding member as in an indirect assay.

32. The method according to claim 29, wherein said capture reagent is attached to a solid phase material.

33. The method according to claim 32, wherein said solid phase material is selected from the group consisting of magnetic particles, polystyrene beads, microtitre plates, nitrocellulose, polystyrene tubes, glass tubes, agarose, polyacrylamide beads and silicon particles.

34. The method according to claim 32, wherein said solid phase material is selected from the group consisting of microparticles and protein binding membranes.

35. The method according to claim 32, wherein said solid phase material is a porous, bibulous, absorbent or capillary material.

36. The method according to claim 29, wherein said capture reagent is attached to a plurality of microparticles, and wherein said microparticles are retained by a solid phase base material.

37. The method according to claim 29, wherein said capture reagent is attached to a carrier material.

38. The method according to claim 37, wherein said carrier material is bovine serum albumin.

39. The method according to claim 29, wherein at least one of said capture reagent and said indicator reagent is specific for at least one ancillary specific binding member.

40. A test kit for determining the presence or amount of an analyte in a test sample, comprising:

a. an indicator reagent comprising an organic polymer latex particle prepared from the polymerization of a plurality of nonchromophoric monomers, said particle selected from the group consisting of poly(pyrrole), polyphenylene, poly(aniline), poly(thiophene), poly(naphthalene), poly(thiophenol) polyacetylene and derivatives thereof, and having light absorbance characteristics resulting from a conjugated structure from the polymerization of said monomers wherein said polymer latex particle exhibits increased absorbance in the visible spectrum compared to the absorbance in the visible spectrum of the aggregate of nonchromophoric monomers from which it is prepared, said indicator reagent being directly or indirectly attached to a specific binding member and capable of producing a detectable signal indicative of the presence or amount of an analyte in a test sample; and b. one or more assay components including capture reagents, ancillary binding members, solid phase material, buffers, water, stabilizers, surfactants, standards and calibrators.

* * * * *